(12) United States Patent
DeVincenzo

(10) Patent No.: US 6,896,514 B2
(45) Date of Patent: May 24, 2005

(54) ORTHODONTIC IMPLANT

(76) Inventor: John DeVincenzo, 1312 Garden St., San Luis Obispo, CA (US) 93401

( * ) Notice: Subject to any disclaimer, the term of this patent is extended or adjusted under 35 U.S.C. 154(b) by 0 days.

(21) Appl. No.: 10/618,347

(22) Filed: Jul. 14, 2003

(65) Prior Publication Data

US 2004/0166461 A1 Aug. 26, 2004

Related U.S. Application Data

(60) Provisional application No. 60/449,171, filed on Feb. 20, 2003.

(51) Int. Cl.$^7$ ............................. A61C 7/00; A61C 13/12
(52) U.S. Cl. ............................. 433/24; 433/18; 433/172
(58) Field of Search ................................. 433/172, 173, 433/174, 175, 176, 18, 24

(56) References Cited

U.S. PATENT DOCUMENTS

| 4,600,388 | A | * | 7/1986 | Linkow | 433/176 |
|---|---|---|---|---|---|
| 5,836,768 | A | * | 11/1998 | Huskens et al. | 433/173 |
| 6,193,509 | B1 | * | 2/2001 | DeVincenzo | 433/18 |
| 2001/0005575 | A1 | * | 6/2001 | Kanomi et al. | 433/18 |
| 2002/0127510 | A1 | * | 9/2002 | Kyung et al. | 433/18 |
| 2002/0150856 | A1 | * | 10/2002 | Payton | 433/8 |
| 2002/0182560 | A1 | * | 12/2002 | Park et al. | 433/18 |
| 2003/0044746 | A1 | * | 3/2003 | Marotta et al. | 433/18 |
| 2004/0023182 | A1 | * | 2/2004 | Lin | 433/18 |
| 2004/0067464 | A1 | * | 4/2004 | Lin | 433/18 |

* cited by examiner

Primary Examiner—Cary E. O'Connor
(74) Attorney, Agent, or Firm—Rodgers & Rodgers

(57) ABSTRACT

An orthodontic implant having a pair of cross members with an anchoring block disposed thereon, the uppermost of the anchoring block being disposed in a cap, and a wire extending from the cap and being attached to an archwire by an elastic.

9 Claims, 2 Drawing Sheets

ORTHODONTIC IMPLANT

The benefits under 35 U.S.C. 119 are claimed of provisional patent application 60/449,171 filed Feb. 20, 2003.

BACKGROUND OF THE INVENTION

Implants in dentistry have been used for a considerable time, and one of the first clinical examples of their use as an orthodontic anchor was presented by Creekmore[1]. Since that time, a number of investigators have presented modifications of the Creekmore implant including Kanomi in 1997[2], Melsen et al. in 1998[3], Mazzocchi and Bernini in 1998[4], Roberts et al. in 2000[5], Park et al. in 2001[6], Chung et al in 2002[7] and Maino et al in 2003[8]. In all of these embodiments, single screw type implants are placed in buccal or labial positions which then can be used to apply a force to intrude, protract or retract one or more teeth within the same dental arch. This force is generated by attaching a spring or elastomeric material from the implant to the teeth to be moved. The resultant force vector will assure the movement of teeth along this vectorial line. However, should it not be desirable to move teeth in this direction, changes in this vector cannot be accomplished.

Heretofore, it has not been possible to apply a force at some distance from the emergence of the implant from the soft tissue. That is, the location where the anchor emerges from the bone or gingiva has always been used as the point of attachment or resistance of force from the anchor to some distant tooth or teeth.

To alter the direction of this force from the implant to a point distant therefrom has not been proposed nor is it possible to accomplish with a simple screw implant. This becomes readily apparent when one considers the great moments which would be generated if a lever arm extension projected from the screw implants. The screw would tend to rotate easily as the length of the arm increased thereby increasing the moment.

The onplant, first described by Block and Hoffman, can withstand torquing moments but it cannot be placed anywhere except in the palate. Its bulk and thickness require that it be covered by palatal mucosa, but the thin mucosa covering the buccal bone in the vestibules of both the maxillary and mandibular arches is not conducive to the placement of this type anchor.

Thus, mechanisms to intrude individual teeth or to move teeth anteriorly or posteriorly from the screw are available but there has been no ability to manipulate the direction of the force vector or to apply the force at some distance remote from the implant. Additionally it has not been possible with current implant technology to impact an entire dental arch with favorable and varying force vectors whose directions can be changed easily at the discretion of the clinician. Furthermore, it has not been possible, prior to this invention, to extrude individual or groups of teeth.

Implants that would permit force application to be some distance from the center of insertion of the implant could be skeletal implants as used in surgical procedures. The use of these skeletal implants for the movement of teeth was presented by Umerori et al. in 1998[9]. With these skeletal implants, the posterior dentition was intruded but there was no mechanism by which the intrusion force could be delivered selectively to different parts of the dentition, i.e., there was no ability to deliver a pure intrusion force component to any part of the dentition without an accompanying and often undesirable horizontal component. The extrusion of teeth was not possible nor considered by the presentation of Umerori. Thus, at present, there is no mechanism by which the clinician can easily deter or manipulate the direction of force from an implant to one or more teeth.

SUMMARY OF THE INVENTION

By this invention, the surgeon places an implant in as close approximation to the desired position for intrusion or extrusion of teeth as directed by the orthodontist. When the patient returns for orthodontic force applications, an attachment is cemented to the emerging portion of the implant so that forces can be applied with desirable and variable vectors as determined by the clinician. Intrusion or extrusion forces, as they begin to be expressed, will result in certain teeth being moved more than other teeth. The point of force application can then be altered to suit the clinician so that uniform vertical movement of all the teeth in the arch can be accomplished. After the desired vertical movement has been obtained, holding of these gains can be achieved by attachments along the archwire or from attachments directly to the teeth from either the cemented attachment or a wire extending therefrom.

This procedure for vertical and sagital manipulations of the maxillary and/or the mandibular dentitions to facilitate major changes in facial form may require up to four posterior and two anterior implants.

DETAILED DESCRIPTION OF THE INVENTION

Figure 1:
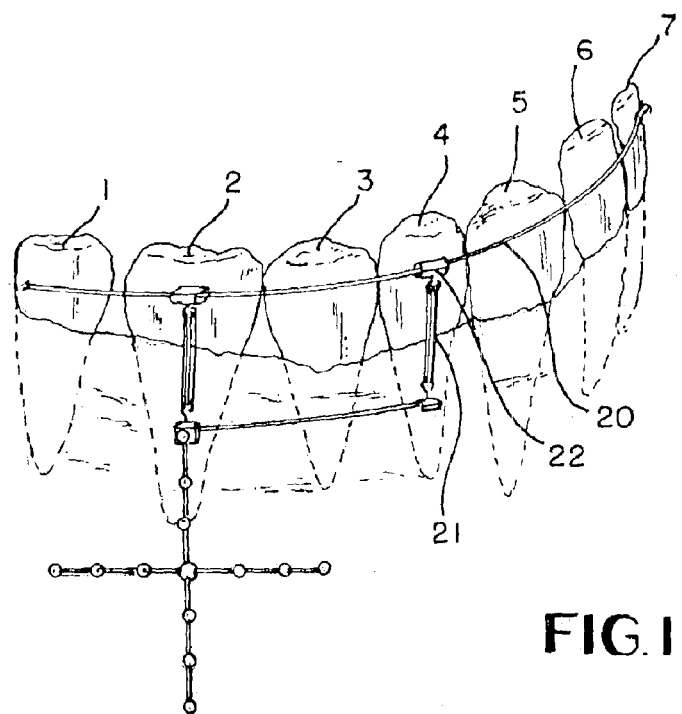
FIG. 1 is a perspective view depicting the orthodontic implant according to this invention as used in the mandibular arch.
Figure 2:
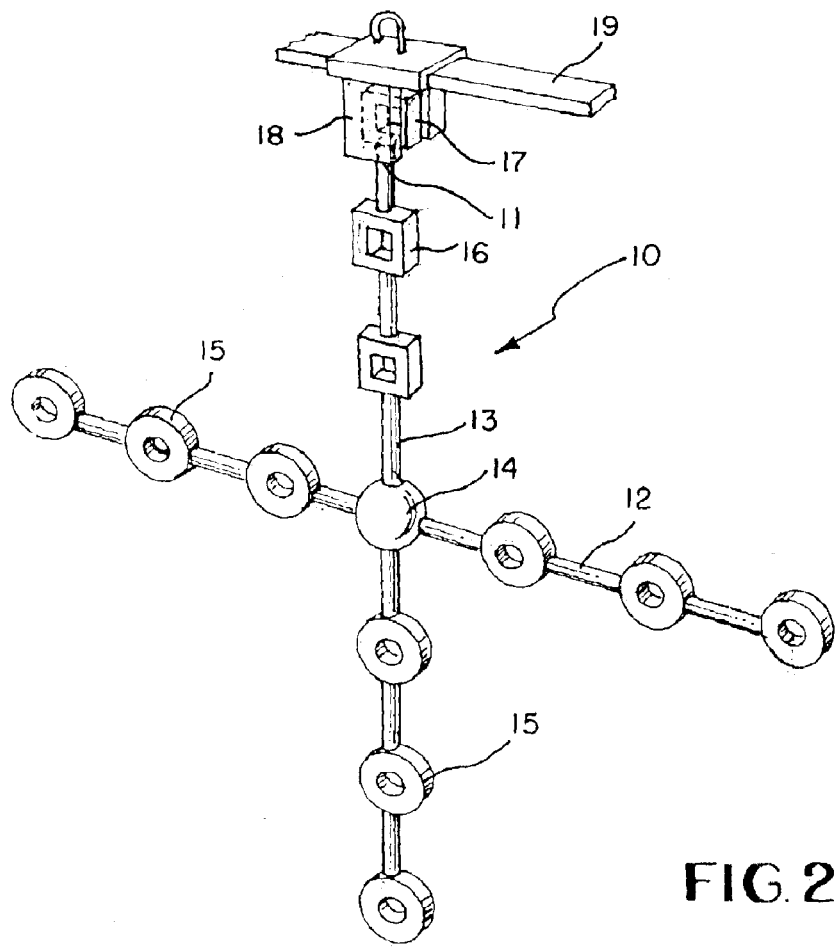
FIG. 2 is an enlarged perspective view of the implant.

In the drawings and with particular reference to FIG. 1, the numerals 1 and 2 designate molars and the numerals 3 and 4 identify bicuspids. To complete the identification of the remainder of teeth shown in FIG. 1, there are cuspid 5 and incisors 6 and 7. By this invention, as depicted in FIG. 1, teeth are intruded or moved downwardly. Each of the teeth 1–7 has a resistance to movement which is related to many factors, one of which involves the root surface area of the teeth to be moved. For instance, the root surface area of tooth 1 is less than the root surface area of tooth 2 and the root surface areas of teeth 3 and 4 are less than the root surface area of tooth 5. Tooth 5, the canine, is a very large rooted tooth and teeth 6 and 7 are lower incisors which have considerably smaller tooth surface areas. Varying responses to movement derived from the implant forces will occur depending on root size and surface area. Additional variability in the movement of the tooth/teeth to forces relate to the position of the root relative to the bone.

Figure 3:
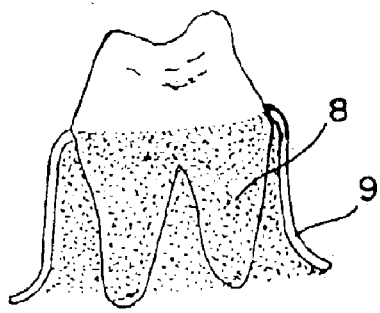
FIGS. 3 and 4 are elevational views showing a tooth root and surrounding bone.
Figure 4:
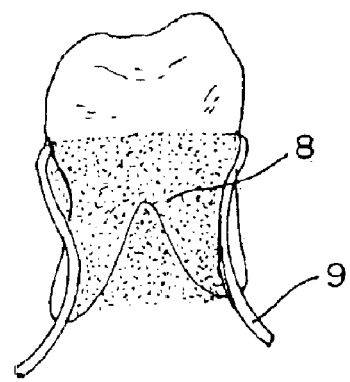

As depicted in FIG. 3, the root is positioned within spongy bone 8, and does not touch the outer thick layer of cortical bone 9. In FIG. 4, the roots of the tooth are protruding through the more metabolically inactive outer cortical bone and are not totally immersed in alveolar or spongy bone 8. The tooth shown in FIG. 3 will move considerably faster than the tooth shown in FIG. 4. The metabolic activity of alveolar or spongy bone is considerably greater than the metabolic activity of cortical bone and this, coupled with the amount of resistance based on root surface area, will have considerable influence on the rate of tooth movement.

Because of these and other variables, it is clinically impossible to predict precisely where implants should be placed. If an implant were placed closer to tooth 1, more vertical movement would incur in that region than if the implant were placed between teeth 4 and 5. If the implant were placed closer to teeth 3 and 4 or between 4 and 5, more vertical movement would occur in that area. It is clinically important to be able to control and manipulate the vertical and sagital positions of all teeth. For example, assuming intrusion of teeth is desired, if certain teeth are intruded more rapidly than others, a tilt to the occlusal plane will result. The clinician needs to have the ability to vary the direction of the force to any place along the arch so that as certain teeth are intruded more quickly, force can be relocated to the other teeth, which are moving more slowly, to equalize intrusion movement. Currently, this can be accomplished only by placing an implant between each tooth within the dental arch which presents considerable additional risk and expense.

By this invention, an implant generally identified by the numeral 10 is positioned by the oral surgeon during an operative procedure and which emerges from the bone at a location identified by the numeral 11. From point 11, force can be applied to teeth 1–7. Although the implant 10 is shown in the drawings as being cross-shaped, it could take the form of an L, I or inverted T.

Implant 10 includes cross members 12 and 13 extending outwardly from attachment point 14. Positioned along cross member 12 and along the lower extension of cross member 13 are multiple anchoring rings 15 which permit the implant to be secured in place by screws as is well known. The upper portion of cross bar 13 includes square anchoring blocks 16 which are angular in configuration for enhanced resistance to torque forces. The uppermost anchoring block 17 is disposed within cap 18 and cap 18 is appropriately cemented into position. Angular extension wire 19 extends from an angular slot in cap 18 which allows the application of forces at various positions along archwire 20 by means of elastic 21 and coupling tube 22, if intrusion movement is desired. Also elastic 21 can be attached directly to archwire 20.

Figure 5:
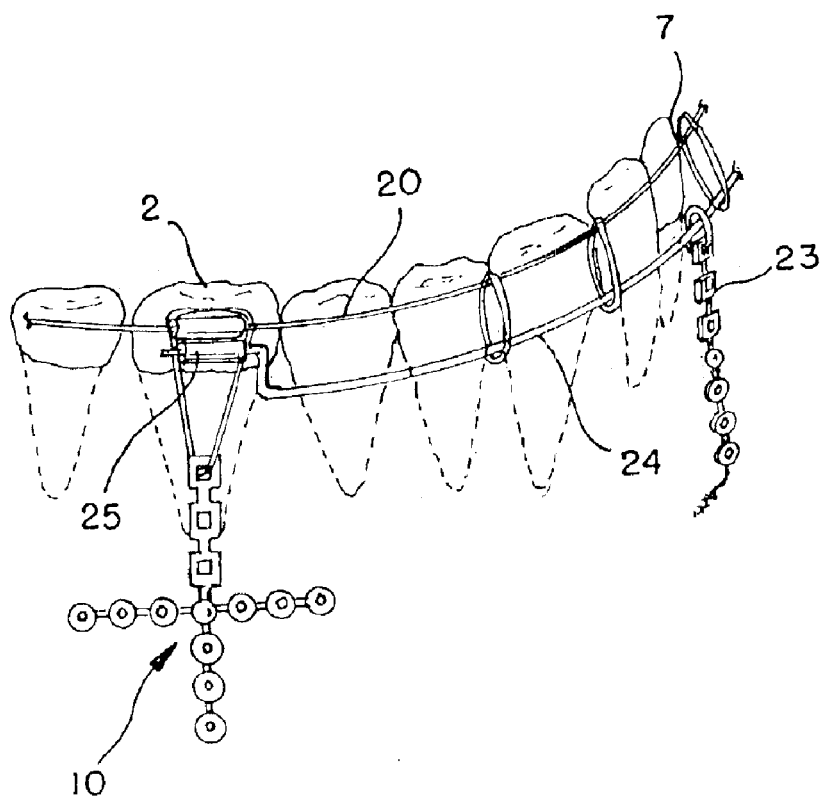
FIG. 5 is a perspective view of a modification of the invention shown in FIG. 1.

Also, as shown in FIG. 5, a second implant 23 in the anterior region can be placed near tooth 7 which would provide a three point contact capability with two posterior implants and one anterior implant. A large round wire 24 extends from tubes 25 attached to the molar and is further stabilized by the anterior implant therefrom and from which forces could be applied to archwire 20. Of course, all the aforementioned discussion is equally applicable to maxillary teeth.

To accomplish vertical extrusion movement of one or more teeth, the flexible, elastic material 21 used to obtain intrusion is replaced by rigid metal extensions connecting large wire 24 directly to teeth or to archwire 20. The configuration of these rigid extensions can be in the form of an S or tooth loop as is understood by the practicing orthodontist. Attachment to the tooth can be through the bracket or to large wire 24 utilizing a tube or cap previously attached to large wire 24.

Therefore, force can be applied at any location along large wire 24 to facilitate selective vertical or sagital movement of different teeth. Although this requires an additional implant, often it permits more rapid and controlled movement of any tooth or combination of teeth in the arch.

BIBLIOGRAPHY

1. Creekmore T D, Eklund M K. The possibility of skeletal anchorage J. clin. Orthod 17:266–9,1983.
2. Kanomi R. mini-implants for orthodontic anchorage. J. clin. Orthod 31:763–7, 1997.
3. Melsen B, Petersen J K, Costa A. Zygomatic ligatures an alternative form of maxillary anchorage. J. clin. Orthod 32:154–8, 1998.
4. Mazzorchi A R, Bernini S. Osseointegrated implants for maximum orthodontic anchorage. J. clin. Orthod 32:412–5, 1998.
5. Roberts W E, Nelson C L, Goodacre C J. Rigid implant anchorage to close a mandibular molar extraction site. J. clin. Orthod 28:693–704, 2000.
6. Park, H S Bae S M, Kyung H M, Sung J H. Micro-implant anchorage for treatment of skeletal class I bialveolar protrusion. J. clin. Orthod 35:417–22, 2001.
7. Chung K R, Kim Y S, Linton J L, Lee Y J. The miniplate with tube for skeletal anchorage . J. clin. Orthod 36:407–12, 2002.
8. Maino G B, Bednar J, Pagin P, Mura P. The spider crew for skeletal anchorage. J. clin. Orthod 37:90–7, 2003.
9. Umerori M, Sugawara J, Mitani H, Nagasaka H, Kawamura H. Skeletal anchorage system for open-bite correction. Am. J. Orthod Dentofac Orthop 115:166–74, 1998.
10. Block M S, Hoffman D R. A new device for absolute anchorage for orthodontics. Am. J. Orthod Dentofac Orthop 107:251–8, 1995.

What is claimed is:

1. A method of applying force to a distant tooth comprising the steps of placing an implant in a patient's mouth, having a portion of said implant extending from the patient's bone, said portion extending from bone being at least partially enclosed in a cap, extending a wire from said cap, securing said wire to a patient's tooth or archwire remote from said cap, placing multiple implants in the patient's mouth one of which is anterior and one or more of which are posterior, connecting said posterior implants and said anterior implant by means of a second wire so that a variety of forces can be applied from any location on said second wire to the patient's tooth or teeth.

2. An orthodontic implant comprising a pair of vertical and horizontal cross members intersecting at an attachment point, anchoring means disposed on said cross members, an anchoring block disposed on the upper end of said vertical member, and a cap enveloping said anchoring block.

3. An orthodontic implant according to claim 2 wherein a wire extends from said cap.

4. An orthodontic implant according to claim 3 wherein an archwire is attached to a patient's teeth and wherein said wire extends horizontally from said upper portion and is attached to said archwire.

5. An orthodontic implant according to claim 4 wherein said archwire and said wire are spaced from each other.

6. An orthodontic implant according to claim 2 wherein multiple circular anchoring means are disposed along a portion of said cross member extending horizontally from said attachment point and extending vertically downwardly from said attachment point.

7. An orthodontic implant according to claim 2 wherein said anchoring block is secured to said cap by means of cement.

8. An orthodontic implant according to claim 2 wherein an angular slot is formed in said cap.

9. An orthodontic implant comprising a pair of vertical and horizontal cross members intersecting an attachment point, anchoring means disposed on said cross members, the upper portion of said vertical cross member being secured to a cap, a wire secured to the upper portion of said member and extending from said upper portion, and the uppermost anchoring means on said vertical cross member being angular in configuration and secured to said cap.

* * * * *